(12) United States Patent
Perrier et al.

(10) Patent No.: US 6,703,490 B1
(45) Date of Patent: Mar. 9, 2004

(54) AMPHIPHILIC COMPLEXES, METHOD FOR THEIR PREPARATION AND COMPOSITIONS CONTAINING THEM

(75) Inventors: Eric Perrier, Vienne (FR); Alain Huc, Foy les Lyon (FR); Danielle Antoni, Vernaison (FR); Coralie Roussel, Perols (FR); Michel Pina, Montpellier (FR); Jean Graille, Maguelonne (FR)

(73) Assignee: Coletica, Lyons (FR)

( * ) Notice: Subject to any disclaimer, the term of this patent is extended or adjusted under 35 U.S.C. 154(b) by 0 days.

(21) Appl. No.: 08/877,124

(22) PCT Filed: Oct. 16, 1996

(86) PCT No.: PCT/FR96/01620
§ 371 (c)(1),
(2), (4) Date: Jun. 17, 1997

(87) PCT Pub. No.: WO97/14713
PCT Pub. Date: Apr. 24, 1997

(30) Foreign Application Priority Data

Oct. 17, 1995 (FR) .............................. 95 12137

(51) Int. Cl.$^7$ .................. C07K 1/113; C07K 14/415
(52) U.S. Cl. ...................................... 530/402
(58) Field of Search ................ 530/402, 345; 435/188

(56) References Cited

U.S. PATENT DOCUMENTS

| 4,234,475 | A |   | 11/1980 | Sokol |
| 4,659,740 | A | * | 4/1987 | Usher |
| 5,071,960 | A |   | 12/1991 | Turowski et al. |
| 5,212,235 | A | * | 5/1993 | Nestaas et al. |
| 5,262,525 | A | * | 11/1993 | Bonnaffé et al. |
| 5,422,111 | A |   | 6/1995 | Huc et al. |

FOREIGN PATENT DOCUMENTS

| EP | 0283601 |   | 9/1988 |
| EP | 368823 A2 | * | 5/1990 |
| EP | 458167 A1 | * | 11/1991 |
| EP | 480901 A1 | * | 4/1992 |
| EP | 505267 A1 | * | 9/1992 |
| WO | WO 93 22370 |   | 11/1993 |

OTHER PUBLICATIONS

Kito, M., "Chemical and Physical Lipophilization of Proteins" (Dec., 1987) J. Amer. Oil Chem. Soc., 64(12), 1676–1681.*
Nishimura et al., "Autoacylation of Soy Proteins" (1989) J. Agric. Food Chem., 37(5), 1266–1270.*
Akita et al., "Lipophilization of β–Lactoglobin Effect on Allergenicity and Digestibility" (1990) J. Food Sci., 55(3), 718–723.*
Ekrami et al. "Water–Soluble Fatty Acid Derivatives as Acylating Agents for Reversible Lipidization of Polypeptides" (Sep. 11, 1995) FEBS Lett., 371(3), 283–286.*
Haque et al., "Lipophilization of β–Lactoglobulin: Effect on Allergenicity and Digestibility" (1983) J. Food Sci., 55(3), 718–723.*
Creuzenet et al. "Acylation and Alkylation of Bovine β–Lactoglobulin in Organic Solvents" (1992) J. Agric. Food Chem., 40(2), 184–190.*
Haque et al., "Lipophilization of Soybean Glycinin: Covalent Attachment to Long Chain Fatty Acids" (1982) Agricultural and Biological Chemistry, 46(2), 597–599.
Haque et al., "Incorporation of Fatty Acid into Food Protein: Palmitoyl Soybean Glycinin" (1982) Journal of Agricultural and Food Chemistry, (30) 481–486.

* cited by examiner

Primary Examiner—Jon P. Weber
(74) Attorney, Agent, or Firm—Merchant & Gould P.C.

(57) ABSTRACT

Cosmetic and pharmaceutical compositions comprising amphiphilic or hydrolipidic complexes of plant proteins modified with fatty chains are presented. The modified proteins are obtained from the reaction carried out at a temperature between ambient temperature and 80° C. with plant proteins having an average molecular mass is greater than or equal to 10,000 Daltons and one or more fatty chains whose carbon atom number is between 4 and 30, selected from fatty acid anhydrides and fatty acid halides, with the exclusion of undecylenic acid.

62 Claims, No Drawings

AMPHIPHILIC COMPLEXES, METHOD FOR THEIR PREPARATION AND COMPOSITIONS CONTAINING THEM

This application is a 371 of PCT/FR96/01620, filed Oct. 17, 1996, which claims priority to a French application Serial No. 95-12137, filed Oct. 17, 1995.

The first object of the present invention is amphiphilic (hydrolipidic) complexes and more specifically proteins (and polypeptides) onto which fatty chains have been grafted. Said complexes may be qualified lipophilised proteins (and polypeptides). Other objects of the present invention are compositions, notably cosmetic, pharmaceuticals or food compositions which contain such complexes and methods for the preparation of said complexes.

The skin may be considered as an organ which separates and protects the human body from its environment. This effect of a barrier against external damaging effects is capital in order that the internal tissues suitably exert their function. External damaging effects are in fact many: luminous damaging effects (UVA, UVB, infra-red) which cause free radicals and fragmentation of the constituents of the skin, physical or mechanical damaging effects (abrasions, variations in temperature and hygrometry . . . ) which cause inflammations, chemical damaging effects (air and water pollution, contact with irritant or immunogenic elements), microbiological damaging effects (bacteria, viruses, fungi . . . ). In order to react to these various damaging effects, the skin possesses a certain number of specialised cells which sometimes form extremely well-characterised structures. This is the case of the corneocytes which, being different from keratinocytes, form a structure called the Stratum corneum which is specialised in the protection of the most internal areas of the skin. This superficial horny structure is the first protection against external damaging effects.

The use of cosmetic products and notably of hydration products also comes up against this natural barrier:
  due to their small size, hydrophilic molecules of low molecular mass such as urea, lactic acid, amino acids, can penetrate via the Stratum corneum as far as in the deepest layers of the cutaneous tissues. The cosmetic effect obtained is a hydrating effect upon the deep layers of the epidermis and the dermis, an effect which is relatively short lived;
  on the contrary, molecules of higher molecular mass such as proteins for example cannot cross this barrier. The Stratum corneum is in fact principally constituted of lipids (its lipid content neighbours 80% by weight), giving it a particularly hydrophobic character, totally incompatible with the hydrophilic character of most proteins used in the cosmetology field. In this case, the cosmetic effect obtained is a filmogenic effect, at times interesting for obtaining particular textures or "cosmetic feels" but which remains totally and exclusively superficial.

Thus, and consequently, the hydrophilic molecules used to this day in cosmetics are cast aside by this hydrophobic structure and either stay on the surface or penetrate the dermis very deeply. From this, the horny layer and the upper layers of the epidermis are under practically no influence of the active and notably hydrating substances used up to this day in cosmetics. Now, the feeling of dryness of the skin comes from the Stratum corneum and upper layers of the epidermis. It is therefore of utmost importance to manage efficiently hydrating this structure and more generally to render said structure accessible to various hydrophilic entities.

The Applicant, within the context of the present invention, has taken on this technical problem of hydration of the skin and more generally that of the optimisation of the expression of the activity of molecules of the protein or polypeptide type upon the Stratum corneum. In order to solve said technical problem, the Applicant proposes modifying the physico-chemical character of said molecules and to thus modify the behaviour of it. The Applicant proposes in fact to generate amphiphilic complexes by grafting fatty chains onto said molecules. The trans-epidermal penetrations of such complexes are different from those of the non-complexed molecules. Their stabilisation in the upper layers of the epidermis as well as on the capillary fibre (hair) has been demonstrated. Furthermore, very interesting and unexpected cosmetic even therapeutic effects of said complexes have been observed.

It has been described in the patent application FR-A-2 671 725 about polyose-fatty acid complexes which have hydrating and emulsifying properties. These complexes are obtained by reacting, in aqueous medium, at ambient temperature, fatty acids in a reactive form with polyoses. Said polyoses can intervene in an impure form and notably in a mixture with proteins. However, in this document, no mention is made of a "binary" protein-fatty acid complex and of the interesting properties it could have . . . In any case, the polysaccharides (polyoses) having a gellifying power much greater than that of proteins, obtaining hydrating and emulsifying complexes by liophilising such proteins could not be expected. Such is all the same one of the results obtained within the context of the present invention.

It has also been described:
  in the patent U.S. Pat. No. 4,234,475 a method of preparing emulsifying agents which consists in reacting, at temperatures above 200° C., a protein and an acid, notably a fatty acid. At such temperatures, the degradation of each one of the reagents cannot be prevented, and notably the degradation of the protein (denatured and/or hydrolysed into peptides), whose properties are consequently inescapably altered;
  in the application WO-A-93 22370 undecylenic acid derivatives obtained by reacting said acid in a reactive form, in an aqueous medium, at ambient temperature with a hydrophilic organic macromolecule having primary alcohol groups and/or primary amine groups, and notably with a protein. Said derivatives, very slightly fragrant, have conserved anti-fungal and anti-bacterial properties. By their approach, the expression of the activities of undecylenic acid have been above all sought-after.

Furthermore:
  the application DE-A-34 22 496 describes an alcoholic disinfectant composition for the skin. Said composition contains a protein hydrolysate, a mixture of amino acids in fact,
  the application EP-A-0 417 619 proposes, as a detergent showing a lesser agressivity towards the skin and the mucous membranes, the condensation products resulting from the chemical reaction between:
    a hydrolysate of proteins whose average molecular mass is between 3,000 and 7,000; and
    a $C_{12}$–$C_{18}$ fatty acid; said chemical reaction being carried out at a pH between 7 and 12 and the protein(s)/fatty acid(s) molar ratio ranging from 1/0.5 to 1/3;
  the application EP-A-0 283 601 describes elastin derivatives prepared from hydrolysed elastin. Said derivatives result from a chemical coupling between said hydrolysed elastin (non-native) and a fatty acid anhydride; said fatty acid intervening, with respect to the protein (hydrolysed elastin) in a weight ratio very much lower than 1.

Said condensation products according to EP-A-0 417 619 and elastin derivatives according to EP-A-0 283 601 are not complexes within the sense of the invention. Said complexes of the invention are always elaborated in the presence of an excess of fatty acid and can be elaborated with native proteins. This is explained below.

DETAILED DESCRIPTION OF THE INVENTION

The Applicant in fact proposes novel amphiphilic or hydrolipidic complexes—protein(s)/fatty chain(s) complexes—which, as indicated above, have very interesting and relatively unexpected cosmetic even therapeutic properties.

It is herein specified that, in the present text—within the context of the present invention—the term protein is used to designate a "real" protein as well as a polypeptide (obtained eventually by synthesis).

Said complexes of the invention are, in a characteristic way, obtained from the reaction carried out at a temperature between ambient temperature and 80° C. between:
 on the one hand, one (or more) protein(s), whose average molecular mass is greater than or equal to 5,000 Daltons; and
 on the other hand, one (or more) fatty chain(s), whose carbon atom number is between 4 and 30, selected from fatty acids, fatty alcohols, fatty amines and derivatives thereof, with the exclusion of undecylenic acid, the [protein(s)/fatty chain(s)] weight ratio ranging from 1/1 to 1/10 and advantageously from 1/3 to 1/5.

The reaction carried out for the coupling and/or grafting of the reagents may be chemical or enzymatic. This shall be specified further or in the present text. In any case, the reaction is carried out a temperature much lower than 200° C., preferably lower than 100° C. The minimisation even prevention of any degradation of the reagents and notably the intervening proteins is desired.

Said reaction is carried out with two types of reagent: on the one hand, at least one protein, on the other hand at least one fatty chain. Said fatty chains consist of fatty acids as well as fatty alcohols or fatty amines (or the derivatives of said acids, alcohols and amines).

The multiplicity and the variety of the complexes of the invention may already be insisted upon and therefore the properties that they may have; the latter depending upon the nature of the reagents (intervening protein(s) and fatty chain(s) and of their intrinsic characteristics (for example, the nature of the intervening protein, the purity of it, the molecular weight of it).

Each one of both types of reagent is specified below.

The complexes of the invention are complexes of proteins and fatty chains. The complexes obtained from amino acids are excluded from the context of said invention, whether they be purified or obtained in a mixture during the hydrolysis of a protein, as well as the complexes obtained from peptides having only 2 to 5 amino acids in their structure. The proteins which can intervene in the structure of the complexes of the invention have an average molecular mass equal to or greater than 5,000 Daltons. They consist of a chain of amino acids linked to each other by amide bonds, which has pendant amine and/or acid and/or alcohol functions.

Generally, their average molecular mass is lower than 1,000,000 Daltons. It is however in no way excluded to prepare complexes of the invention with proteins of a greater average molecular mass. Advantageously, the complexes of the invention are prepared from proteins whose average molecular mass is between 10,000 and 1,000,000 Daltons. Even more advantageously, proteins whose average molecular mass is between 20,000 and 300,000 Daltons are brought in.

In any case, the intervening proteins can be obtained by an extraction which does not destroy their structure and/or does not lower their molecular mass, or by moderate physical, chemical or enzymatic hydrolysis (said hydrolysis generating proteins whose average molecular mass is at least equal to 5,000 Daltons).

Said intervening proteins may be of animal origin (bovine, ovine, fish, shark, crustaceans, . . . ) and in this case, they may be extracted from various tissues; collagen, gelatine, albumin, ovalbumin, elastin, reticulin, fibronectin, keratin, silk, laminin, desmosin and isodesmosin, extracellular matrix proteoglycans, caseins, lactalbumin, lactoglobulins, enzymes extracted from animal tissues, etc . . . may be cited by as examples. They may be of plant origin (wheat, unicellular or multicellular algae, maize, pea, lupin, . . . )and in this case, they may be extracted from seeds, flowers, fruits, barks, gums, etc . . . ; moderated wheat, maize, cotton, lupin, pea, broad bean, almond, bean, soya, sunflower, lucerne, or oat hydrolysates or proteins, etc . . . may be cited for example.

Complexes of the invention are advantageously prepared with soya, wheat, oat or almond proteins.

As regards the second type of reagent, these are as already specified, fatty chains having from 4 to 30 carbon atoms. Advantageously, the intervening fatty chains have from 6 to 20 carbon atoms. The chains may be saturated or unsaturated, linear, branched or cyclic. They obviously have acid and/or alcohol and/or amine functions but it is in no way excluded that they have other chemical functions in their structure which intervene or do not intervene in the preparation of the complexes of the invention.

Said fatty chains may notably be selected from the heptanoic, octanoic, decanoic, lauric, myristic, palmitic, stearic, ricinoleic, oleic, linoleic, linolenic fatty acids; the corresponding fatty alcohols and fatty amines; the derivatives of said fatty acids, fatty alcohols and fatty amines; and mixtures thereof.

Advantageously, complexes of the invention are prepared:
 with lauric, stearic or palmitic acids and notably a mixture of stearic and palmitic acids;
 with laurylamine or hexadecylamine;
 with decylalcohol.

It has been seen that said fatty chains consist of fatty acids, fatty alcohols or fatty amines (or their derivatives). For the preparation of the complexes of the invention chemically, said fatty acids optionally intervene in reactive forms (more reactive), and notably as halides (chlorides, bromides, iodides, . . . ), anhydrides or derivatives of anhydrides.

Within the structure of the complexes of the invention, the [protein(s)]/[fatty chain(s)] weight ratio ranges from 1/1 to 1/10 and preferentially from 1/3 to 1/5.

The protein(s) are in fact always allowed to react with a more or less large excess of fatty chain(s) with the aim of creating covalent bonds but also of the ionic, hydrogen and Van der Waals type.

Generally and furthermore, at the end of the reaction, the unreacted fatty chains which are not bound to the protein are not recovered, the isolation of "binary" complexes of the pure protein(s)-fatty chains type is not attempted. Thus, the complexes of the invention generally consist of "binary" complexes of the type indicated above in a mixture with non-bound fatty chains; in other words, they consist of the product of the coupling reaction in a mixture with unreacted (un-coupled) fatty chains.

Said complexes constitute the first object of the present invention. The compositions, notably cosmetic, pharmaceutical or food compositions, containing them constitute the second object of the said invention.

Said compositions generally contain from 0.01 to 40% by weight of such complex(es) and advantageously from 0.1 to 10% by weight.

More specifically, the notably cosmetic, pharmaceutical or food compositions which contain at least one protein as active ingredient make up an integral part of the present invention; said protein which intervenes, being at least in part (even in totality) as a complex such as described above. For the elaboration of said compositions, said complex may be used purified (isolated from the reaction mixture in which it was synthesised) or as a mixture with one and/or the other of the reagents which intervened in its synthesis. According to this second variant, the reaction mixture (at the end of the reaction) is advantageously used which contains said complex and the unreacted reagents (principally fatty chains insofar as they intervene in excess).

The compositions wherein said complexes intervene as emulsifying agents also make a part of the invention.

In any case, it was noted in a surprising way that the complexes of the invention have hydrating and emulsifying properties. This is relatively unexpected insofar as the person skilled in the art cannot ignore that the proteins have a capacity to trap water which is much lower than that of polysaccharides and insofar as said capacity, which is relatively low in the absolute, should have been affected by the lipophilisation of said proteins.

In addition to these hydrating and emulsifying properties, which are relatively unexpected, the complexes of the invention have revealed to have other properties which are totally unexpected.

It is as such that a soluble wheat protein having an average molecular mass of 100,000 Daltons, onto which stearic and palmitic acid chains have been grafted, have extremely strong skin restructuration properties, which enable one to envisage the use of this lipophilised protein (complex in the sense of the invention) in applications wherein a destructuration of the epidermis is observed (physico-chemical damaging effects or skin ageing . . . ).

Similarly, a soluble almond protein having an average molecular mass of 30,000 Daltons, onto which stearic and palmitic acid chains have been grafted, has the property of calming moderate to strong sunburn, which enables envisaging the use of this lipophilised protein (complex in the sense of the invention) in sun or after-sun formulations.

Similarly, an insoluble laminary protein having an average molecular mass of 10,000 Daltons onto which caprylic acid chains have been grafted has the property of inhibiting a certain number of micro-organisms, which enables one to envisage the use of this lipophilised protein (complex in the sense of the invention) in applications wherein the destruction of micro-organisms is envisaged (anti-acne effects, anti-dandruff effects, anti-body odour effects, natural preservative . . . ).

It has previously been insisted upon the diversity of the complexes of the invention. The interest of such a diversity is herein referred to.

Furthermore, it is recalled herein that the properties of the complexes of the invention, whether they are more or less unexpected, are expressed as expected, on the Stratum corneum, by their lipophilisation.

The compositions of the invention therefore consist essentially of cosmetic compositions. It is not excluded that these are therapeutic, food or dietary compositions which are particularly efficient on the mucous membranes.

According to its third aspect, the invention relates to a method of preparing amphiphilic (hydrolipidic) complexes described above. Said method characteristically comprises the reaction, at a temperature between ambient temperature and 80° C., if need be in aqueous medium or solvent medium, between at least one protein of the aforementioned type and at least one fatty chain of the aforementioned type, said reagents intervening in a [protein(s)/fatty chain(s)] weight ratio between 1/1 and 1/10, advantageously between 1/3 and 1/5. Said reaction may be qualified a grafting reaction or more exactly a coupling reaction (insofar as it does not generate only covalent bonds between the reagents).

Said reaction is carried out at a relatively low temperature. The degradation of the reactive proteins is thus minimised. The reaction brings in or does not bring in a solvent, aqueous medium or organic solvent. The intervention of such a solvent may be done away with if, at the temperature of the reaction, the reagents are liquid.

At the end of the reaction, the "binary" complexes are generally not isolated. They are found thus in a mixture principally with the unreacted fatty chains.

It is generally desired to adjust the pH of the complexes obtained in order to render it compatible with the later, notably cosmetic applications. The pH is adjusted to values between 2 and 10 and more particularly between 5 and 7. To this end, neutralising agents are used which are selected from:

inorganic bases (such as KOH, NaOH, $Ca(OH)_2$. . . );

metal bases (as hydroxide, carbonate . . . );

organic bases (citrate, phosphate, borate, acetate, TRIS . . . buffers; $C_1$–$C_6$ amines or alkylamines: triethanolamine, aminomethylpropane . . . ).

After preparing the complexes whose pH, if need was, adjusted to pHs compatible with their later use (said pH is advantageously adjusted by dispersion of said complexes in the aqueous phase), it is possible to dry them by atomisation, lyophilisation, dehydration under vacuum . . . Said dried complexes, or directly obtained without water, may be then made into a form, notably in the form of turnings.

The coupling reaction carried out may be carried out chemically or enzymatically. The enzymatic route is, within the context of the present invention, totally original.

According to said chemical route, it is possible to:

+react the fatty chains—fatty acids, fatty alcohols, fatty amines—under conventional conditions of peptide synthesis; i.e. in the presence of bifunctional agents, such as diimides;

+react the fatty acids in reactive (more reactive) forms i.e. react halides (chlorides, bromides, iodides . . . ) of fatty acids, fatty acid anhydrides, fatty acid anhydride derivatives . . .

According to said original enzymatic route, the proteins are coupled to the fatty chains in the presence of an enzyme, generally at a temperature between 30 and 70° C. Advantageously said temperature is between 50 and 60° C. Advantageously, the intervening enzyme is an acyltransferase. According to three variants of this enzymatic route, said enzyme is a lipase, notably selected from Mucor miehei lipase, pig pancreas lipase, Rhizopus arrhizus lipase, Candida lipase, Bacillus lipase and Aspergillus lipase, or a protease, notably consisting of papaine, or an amidase. Such an enzymatic reaction ensures, as the chemical reactions recalled above, the grafting of fatty chains onto the proteins. Said fatty chains, when they are fatty acids, can intervene as esters (including esters of glycerides). The enzyme present in the reaction medium ensures, firstly, the transesterification.

The reaction carried out, chemical or enzymatic, ensures the coupling by generating ester and/or amide covalent bonds. It has been seen that said coupling also brings in ionic bonds, hydrogen bonds, Van der Waals type forces . . .

The reaction is advantageously carried out with a water activity of the reaction medium ($a_w$) between 0.2 and 1 and advantageously between 0.3 and 0.7.

The methods of preparing compositions of the invention, notably cosmetic, pharmaceutical and food compositions containing hydrolipidic complexes also make up a part of the invention. They principally consist in mixing the active ingredient with an appropriate excipient. It has been seen that said active principle could have emulsifying properties. This can reveal to be particularly interesting. The intervention of any synthetic emulsifying agent may thus be limited, even eliminated.

The invention is illustrated, under its various aspects, by the Examples below.

All percentages indicated are percentages by weight, unless otherwise indicated.

EXAMPLE 1

Preparation of a Lauric Acid (C12)-Soya Protein Complex.

1,660 g of lauric acid of purity equal to 99% are heated to 60° C. in a reactor under nitrogen. After fusion of the lauric acid chains and obtaining a colourless oil, 470 g of a soya isolate (average molecular weight: 50,000 D), containing at least 96% of native proteins, are then added in a fine stream into the reactor under moderate mechanical stirring.

After a homogeneous suspension is obtained, 300 g of lipase extracted from Mucor miehei, immobilised on macroporous ion exchange resin (commercial name: Lipozyme® from Novo) are added to the reactor. The whole is kept for 15 days at 60° C. in a closed reactor under moderate mechanical stirring.

After 15 days' reaction, the complex is filtered at 90° C. so as to remove the enzyme. The complex thus obtained is made into turnings during its cooling.

After analyses, it proves to be that this complex is constituted of lipophilised proteins of which about 16% of the free amine functions (lateral and terminal) were grafted by the fatty acids (lauric acid).

This complex is a beige powder of turnings of characteristic odour. It may be used in a cosmetic formulation at 3% and, by virtue of the amphiphilicity brought about by the grafting, it is possible to incorporate it in the aqueous and/or oily phases of a cosmetic preparation.

EXAMPLE 2

Preparation of a Stearic (C18) Acid and Palmitic (C16) Acid-soya Protein Complex 270 g of stearic acid and 180 g of palmitic acid, each of greater than 90% purity, are placed in 1,000 ml of tert-butanol, and then heated to 60° C. in a reactor under nitrogen. After fusion of the acid chains and obtaining a colourless oil, 150 g of an soya isolate (average molecular mass: 50,000 D), which contains at least 96% of native proteins, are then added in a fine stream into the reactor under moderate mechanical stirring.

After a homogeneous suspension is obtained, 45 g of lipase extracted from Rhizopus arrhizus are added to the reactor. The whole is kept for 21 days at 55° C. in a closed reactor under moderate mechanical stirring.

After 21 days' reaction, the complex is heated at 90° C. for 20 minutes so as to inactivate any residual enzymatic activity. The tert-butanol is then removed by distillation under reduced pressure. The complex thus obtained is made into turnings during its cooling.

After analyses, it proves to be that the complex is constituted of lipophilised proteins of which about 21% of the lateral amine functions were grafted by the fatty acids.

This complex is a beige powder of turnings of characteristic odour. It may be used in a cosmetic formulation at 3% and, by virtue of the amphiphilicity brought about by the grafting, it is possible to incorporate it in the aqueous and/or oily phases of a cosmetic preparation.

EXAMPLE 3

Preparation of a Stearic (C18) and Palmitic (C16) Acid-wheat Protein Complex

Carried out as described in Example 2 by substituting the 150 g of the soya isolate with 150 g of an atomisate obtained from a solution of wheat protein (average molecular mass: 100,000 D). A complex of the type described in Example 2 is obtained (beige coloured turnings of characteristic odour).

EXAMPLE 4

Preparation of a Stearic (C18) Acid and palmitic (C16) acid-almond Protein Complex.

300 g of stearic acid and 140 g of palmitic acid, each of greater than 90% purity, are placed in 1,000 ml of isopropanol, and then heated to 60° C. in a reactor under nitrogen. After fusion of the acid chains and obtaining a homogeneous oily phase, 150 g of an lyophilisate obtained from a solution of almond protein (average molecular mass: 30,000 D), are then added in a fine stream into the reactor under moderate mechanical stirring.

After a homogeneous suspension is obtained, 35 g of lipase extracted from Rhizopus arrhizus are added to the reactor. The whole is kept for 12 days at 55° C. in a closed reactor under moderate mechanical stirring.

After 12 days' reaction, the complex is heated at 90° C. for 20 minutes so as to inactivate any residual enzymatic activity. The isopropanol is then removed by distillation under reduced pressure. The complex thus obtained is made into turnings during its cooling.

This complex is a beige powder of turnings of characteristic odour. It may be used in a cosmetic formulation at 3% and, by virtue of the amphiphilicity brought about by the grafting, it is possible to incorporate it in the aqueous and/or oily phases of a cosmetic preparation.

EXAMPLE 5

Carried out as described in Examples 2 to 4 but the intervening solvent is selected from hexane, chloroform, cyclohexane, chloromethane, dichloromethane, trichloromethane, diethyl ether, methyl tert-butyl ether, or a mixture of these solvents.

EXAMPLE 6

Carried out as described in the preceding examples but in varying the nature of the enzyme used: Mucor miehei lipase, pig pancreas lipase, Rhizopus arrhizus lipase, Candida lipase, Bacillus lipase, Aspergillus lipase, or other acyltransferases.

EXAMPLE 7

Carried out as described in the preceding examples but in varying the nature of the intervening protein: wheat protein, oat protein, maize protein, almond protein, soya protein.

EXAMPLE 8

Carried out as described in the preceding examples but in varying the parameters of the coupling reaction below:
- the proportion between fatty chains and proteins (or polypeptides);
- the reaction temperature (between ambient temperature and 80° C.)
- reaction time (from 30 minutes to 21 days).

EXAMPLE 9

Carried out as described in the preceding examples but in varying the nature of the intervening fatty acid: heptanoic (C7) acid, octanoic (C8) acid, decanoic (C10) acid, lauric (C12) acid, myristic (C14) acid, palmitic (C16) acid, stearic (C18) acid, ricinoleic (C18) acid, oleic (C18) acid, linoleic (C18) acid, linolenic (C18) acid, other fatty acids with shorter or longer chain saturated, unsaturated or polyunsaturated fatty acids, used pure or as a mixture.

EXAMPLE 10

Carried out as described in the preceding examples but the fatty acids which are reacted with the proteins are in the form of esters, and the lipase used effects a transesterification and/or transacylation reaction. Thus, ethyl linoleate, isopropyl oleate and glycerol linoleate as well as various vegetable oils in the form of triglycerides (of which coconut oil) were used to provide the fatty chain which will then come to graft onto the protein.

EXAMPLE 11

Carried out as described in Examples 1 to 9 but the fatty acids which are reacted with the proteins are in a reactive form, of the type acid halide or acid anhydride. In this case, the reaction can be carried out in water at ambient temperature and does not necessitate lipase. Such reactions are explicitly described in Examples 17 and 18.

EXAMPLE 12

Carried out as described in examples 1 to 8 but the fatty chains which are reacted with the proteins are in the alcohol form (formation of ester bonds with the carboxylic acid functions of the protein) or in the amine form (formation of amide bonds with the carboxylic acid functions of the protein). Such reactions are explicitly described in examples 14 and 16 below.

EXAMPLE 13

Carried out as described in examples 2 to 12 but without using solvent.

EXAMPLE 14

Preparation of a Decyl Alcohol (C10)-soya Protein Complex 300 g of decyl alcohol, of greater than 90% purity, are heated to 60° C. in the presence of 670 ml of tert-butanol in a reactor under nitrogen. After fusion of the decyl alcohol chains and obtaining a colourless oil, 100 g of a soya isolate (average molecular mass: 50,000 D), containing at least 96% of native proteins, are then added in a fine stream into the reactor under moderate mechanical stirring.

After a homogeneous suspension is obtained, 30 g of lipase extracted from Rhizopus arrhizus are added to the reactor. The whole is kept for 10 days at 60° C. in a closed reactor under moderate mechanical stirring.

After 10 days' reaction, the complex is heated at 90° C. for 20 minutes so as to inactivate any residual enzymatic activity. The tert-butanol is then removed by distillation under reduced pressure. The complex thus obtained is made into turnings during its cooling.

After analyses, it proves to be that this complex is constituted of proteins lipophilised with fatty chains, and about 12% of the fatty alcohols were coupled to the protein (with the aid of covalent bonds such as ester functions, but also with the aid of ionic functions).

This complex is a beige powder of turnings of characteristic odour. It may be used in a cosmetic formulation at 3% and, by virtue of the amphiphilicity brought about by the grafting, it is possible to incorporate it in the aqueous and/or oily phases of a cosmetic preparation.

EXAMPLE 15

Carried out as described in the preceding examples but the complexes formed are dispersed in the aqueous phase and their pH is adjusted so as to be compatible with cosmetic formulations, with the aid of an inorganic or organic base. The complexes thus obtained can then be dried by atomisation, lyophilisation or drying under vacuum.

EXAMPLE 16

Preparation of a Laurylamine (Cl2)-soya Protein Complex 300 g of laurylamine, of greater than 90% purity, are heated to 60° C. in the presence of 670 ml of tert-butanol in a reactor under nitrogen. After fusion of the laurylamine chains and obtaining a colourless oil, 100 g of a soya isolate (average molecular mass: 50,000 D), containing at least 96% of native proteins, are then added in a fine stream into the reactor under moderate mechanical stirring.

After a homogeneous suspension is obtained, 30 g of lipase extracted from Rhizopus arrhizus are added to the reactor. The whole is kept for 10 days at 60° C. in a closed reactor under moderate mechanical stirring.

After 10 days' reaction, the complex is heated at 90° C. for 20 minutes so as to inactivate any residual enzymatic activity. The tert-butanol is then removed by distillation under reduced pressure. 4,000 ml of water are then added to the complex and the whole is brought up to 70° C. under moderate stirring; then, about 1.5 moles of HCl (as a 6N solution) are added slowly to the reaction mixture so as to obtain a pH between 5.0 and 7.0. The complex thus obtained is then dried by lyophilisation.

After analyses, it proves to be that this complex is constituted of proteins lipophilised with fatty chains, and about 11% of the fatty amines were coupled to the protein (with the aid of covalent bonds such as ester functions, but also with the aid of ionic functions).

This complex is a beige powder of turnings of characteristic odour. It may be used in a cosmetic formulation at 3% and, by virtue of the amphiphilicity brought about by the grafting, it is possible to incorporate it in the aqueous and/or oily phases of a cosmetic preparation.

EXAMPLE 17

Preparation of a Stearic (C18) and Palmitic (C16) Acids-wheat Protein Complex 100 g of soluble wheat protein of high average molecular mass (100,000 D) extracted from wheat gluten are placed in 5,000 ml of demineralised water. The reaction mixture is adjusted to pH 11 with a sodium hydroxide solution (NaOH, 12N). Under very strong stirring of the Ultraturrax or Silverson type (10,000 to 20,000 rpm), 300 g of a mixture of stearic and palmitic acid chlorides are then added slowly. The pH goes in a few tens of minutes from 11 to neighbouring 1 when a buffer is not added to the reaction mixture. After a reaction time of about one hour at ambient temperature, the whole is neutralised to a pH neighbouring 7.0 with a sodium hydroxide solution (NaOH, 12N). The whole is then lyophilised and then optionally sterilised by gamma or beta rays. The product is a white pulverulent powder which can be placed in both aqueous phases and oily phases of the cosmetic preparations for example. Part of the fatty acids has reacted with the protein to form amide and ester bonds, and a part has not reacted finds itself nevertheless strongly complexed by hydrogen bonds and by Van der Waals forces to the protein.

EXAMPLE 18

Preparation of a Stearic (C18) and Palmitic (C16) Acids-almond Protein Complex

The same technique of grafting is carried out as in Example 17 above, but an almond protein, of average molecular mass near to 30,000 D is used instead of the wheat protein. The reaction is carried out in regulating the pH to 11 by adding sodium carbonate. The complex leaving this grafting is kept in the liquid form and contains 5% dry matter; 0.2% parabens and 0.5% xanthane gum are then added. The complex thus formed is marketed under the form of this solution thus described.

EXAMPLE 19

Carried out as described in examples 17 and 18 but in operating at temperatures between 20 and 100° C. The grafting reactions carried out at very high temperatures give better yields but give rise to moderate to severe degradations of the proteins used.

EXAMPLE 20

Preparation of a Hexadecylamine (C16)-oat Protein Complex 80 g of oat protein of average molecular mass equal to 6,000 D are placed in 4,000 ml of demineralised water. The medium is neutralised to pH 7.0. A sufficient quantity of phosphate buffer is added so as to obtain a 0.5 M phosphate buffer in the reaction medium. 1 mole of a carbodiimide such as for example 190 g of N-(dimethylamino-3-propyl)-N'-ethylcarbodiimide hydrochloride is then added to the mixture under stirring; 240 g of 1-hexadecylamine, beforehand placed in suspension in 2,000 ml of water brought to 80° C., are then added to the reaction mixture under very powerful mechanical stirring (Ultraturrax type, 10,000 to 20,000 rpm). The whole is kept under stirring for 1 hour at ambient temperature or 24 hours at 6° C., and then adjusted to a pH of 7.0. It is then optionally dialysed against distilled water for 48 hours at 6° C., optionally dried by lyophilisation, and then optionally sterilised with beta or gamma rays.

The covalent bond which results from this reaction provides the amide bonds, but other characteristic bonds are present between the fatty amine and the polypeptide, such as ionic bonds and Van der Waals type forces.

Tolerance and Toxicity

Skin and ocular irritation studies (carried out according to the protocols in accordance with the OCDE directives N°404 (May 12, 1981) and N'405 (Feb. 24, 1987)), were carried out with several of the products obtained according to the examples above (Examples 1 to 20) in the form of solutions at 10%. In every case, the products appeared as being "non-irritant" (did not provoke any sign of skin or ocular irritation), and were extremely well tolerated.

Similarly, the administration by the oral route of maximal doses of 5 g of these products per kilogram of body weight did not provoke any toxicity (tests carried out according to a protocol in accordance with the directive line of the OCDE relating to the study of the toxicity by the oral route (No. 401 (Feb. 24, 1987))).

Furthermore, sensitisation tests according to the protocol of Magnusson and Kligman were carried out with these products in solution in water at 10% and these products were classed amongst the products not having a sensitising property.

EXAMPLE 21

Anti-age, Restructuring Formulation CC591

| Phase | Products | INCI names | Quantities (%) |
| --- | --- | --- | --- |
| A | Brij 72 | Steareth 2 | 3 |
| | Brij 721 | Steareth 21 | 2 |
| | Isostearyl Isostearate | Isostearyl Isostearate | 4 |
| | Apricot kernel oil | Apricot Kernel Oil | 4 |
| | Huile de safran | Safflower Oil | 2 |
| | Dimethicone 556 | Dimethicone 556 | 2 |
| | Crodacol CS50 | Ketostearyl Alcohol | 3 |
| B | Water | Water | qs for 100 |
| | Glycerine | Glycerine | 5 |
| | Product of the invention according to example 2 | | 6 |
| C | Phenonip ® | Phenoxyethanol | 0.5 |
| | | Methylparaben | |
| | | Ethylparaben | |
| | | Propylparaben | |
| | | Butylparaben | |
| D | Propylene glycol | Propylene Glycol | 0.5 |
| | Perfume | | 0.3 |
| | Alpha tocopherol | Alpha Tocopherol | 0.05 |

Phases A and B are heated separately under moderate stirring. The pH of phase B is adjusted to the desired value. A is poured into B under very vigorous stirring (Silverson or Ultraturrax type), the temperature is then allowed to drop under slow stirring. At 30° C., the components of phases C and D are added.

EXAMPLE 22

Anti-age Face Formulation CC585

| Phase | Products | INCI names | Quantities (%) |
|---|---|---|---|
| A | Isostearyl Isostearate | Isostearyl Isostearate | 4 |
|   | Huile de Carthame | Safflower Oil | 4 |
|   | Cetiol 3600 | Oleyl Erucate | 2 |
|   | Dimethicone 556 | Dimethicone | 5 |
|   | Crodacol CS50 | Ketostearyl Alcohol | 3 |
|   | Product of the invention according to example 17 | | 3 |
| B | Glycerine | Glycerine | 5 |
|   | Water | Water | qs for 100 |
| C | Phenonip ® | Phenoxyethanol Methylparaben Ethylparaben Propylparaben Butylparaben | 0.5 |
|   | Propylene glycol | Propylene Glycol | 0.5 |
| D | Perfume | Perfume | 0.3 |

Phases A and B are heated separately under moderate stirring. The pH of the formula is conditioned in this case by the pH of the product of the invention. A is poured into B under very vigorous stirring (Silverson or Ultraturrax type), the temperature is then allowed to drop under slow stirring. At 30° C., the components of phases C and D are added. If need be, the preparation is adjusted to the desired pH with the aid of lactic acid for example.

EXAMPLE 23

Dry Skin, Face Formulation

| Phase | Products | INCI names | Quantities (%) |
|---|---|---|---|
| A | Huile de bourrache | Borrage Oil | 2 |
|   | Huile de Carthame | Safflower Oil | 4 |
|   | Myritol 318 | Caprylic/Capric triglyceride | 6 |
|   | Crodacol CS50 | Ketostearyl Alcohol | 3 |
| B | Glycerine | Glycerine | 5 |
|   | Eau | Water | qs for 100 |
|   | Product of the invention according to example 2 | | 4 |
| C | Phenonip ® | Phenoxyethanol Methylparaben Ethylparaben Propylparaben Butylparaben | 0.5 |
|   | Propylene glycol | Propylene Glycol | 0.5 |
| D | Perfume | Perfume | 0.3 |

Phases A and B are heated separately under moderate stirring. The pH of phase B is adjusted to the pH of the formulation desired. A is poured into B under very vigorous stirring (Silverson or Ultraturrax type), the temperature is then allowed to drop under slow stirring. At 30° C., the components of phases C and D are added. If need be, the preparation is adjusted to the desired pH with the aid of lactic acid for example.

EXAMPLE 24

Family Shampoo Formulation

| Phase | Products | INCI names | Quantities (%) |
|---|---|---|---|
| A | Texapon N40 ® (Henkel) | sodium laureth sulphate | 40 |
|   | Comperlan KD ® (Henkel) | Cocamide DEA | 2 |
| B | Product of the invention according to example 17 | | 0.3 |
|   | Water | Water | qs for 100 |
|   | sodium chloride | sodium chloride | 1.5 |
| C | Phenonip ® | Phenoxyethanol Methylparaben Ethylparaben Propylparaben Butylparaben | 0.5 |
|   | Propylene glycol | Propylene Glycol | 0.5 |

Phase B is heated separately at 75° C. under moderate stirring. The pH of said phase B is adjusted to the pH of the formulation desired. B is poured into A at 20° C. under very slow stirring, the temperature is then allowed to drop. At 30° C., phase C is added.

EXAMPLE 25

Mild Shampoo Formulation

| Phase | Products | INCI names | quantities (%) |
|---|---|---|---|
| A | Tween 20 ® (ICI) | Polysorbate 20 | 10 |
|   | TegoBetaine L7 ® (Goldschmidt) | Cocamidopropyl Betaine | 10 |
|   | Atlas G1821 ® (ICI) | PBG-150 Distearate | 3 |
| B | Product of the invention according to example 18 | | 0.5 |
|   | Water | Water | qs for 100 |
| C | Phenonip ® | Phenoxyethanol Methylparaben Ethylparaben Propylparaben Butylparaben | 0.5 |
|   | Propylene glycol | Propylene Glycol | 0.5 |

Phase B is heated separately at 75° C. under moderate stirring. The pH of said phase B is adjusted to pH of the formulation desired. A is homogenised at 20° C. B is poured into A at 20° C. under very slow stirring, the temperature is then allowed to drop. At 30° C., phase C is added.

EXAMPLE 26

Pearlescent Shampoo Formulation

| Phase | Products | INCI names | Quantities (%) |
|---|---|---|---|
| A | | | 40 |
|   | Texapon N40 ® (Henkel) | Sodium Laureth Sulphate | 2 |
|   | Comperlan KD ® (Henkel) | Cocamide DEA | 4 |
|   | Euperlan PK771 ® (Henkel) | Glycol Distearate (and) Sodium Laureth Sulphate (and) Cocamide MEA (and) Laureth-10 | |

15

-continued

| Phase | Products | INCI names | Quantities (%) |
|---|---|---|---|
| B | Product of the invention according to example 16 | | 0.5 |
| | Water | Water | qs for 100 |
| | Sodium chloride | Sodium Chloride | 1.5 |
| C | Phenonip ® | Phenoxyethanol Methylparaben Ethylparaben Propylparaben Butylparaben | 0.5 |
| | Propylene glycol | Propylene Glycol | 0.5 |

Phase B is heated separately at 75° C. under moderate stirring. The pH of phase B is adjusted to the pH of the formulation desired. B is homogenised at 20° C. B is poured into A at 20° C. under very slow stirring and then the temperature is allowed to drop. At 30° C., phase C is added.

EXAMPLE 27

Use of a Stearic and Palmitic Acids-wheat Protein Complex in "Restructuring" Cosmetic Applications and which Enable Fighting against Ageing Effects The complexes prepared out according to Examples 3 (enzymatically) and 17 (chemically) were tested for their capacity to smoothen the skin micro-relief. The outside appearance of the skin does in fact reveal its general state, and the meshes formed by the skin micro-depressionary network have a tendency to grow and to dig in during ageing. Other external factors can also contribute to this phenomenon, as for example the use of detergents. This disorganisation of the micro-relief is the sign of an alteration of the horny layer and of its natural protective barrier function. It gives a rough appearance and a coarse integument touch and then leads to a pronounced dehydration of it.

The restructuring activity of these complexes was studied after an important destruction of the micro-depressionary network obtained by a chemical damaging effect of the skin coating with the aid of an aqueous solution which contains 10% detergent (sodium lauryl sulphate). The tests were carried out on the external side of both hands of 10 volunteers. Each hand was washed 4 times a day for 30 seconds, at ½ hour intervals for 4 days with this detergent solution. One of the hands received at the end of these treatments, each day, a treatment carried out from a solution containing 3% of the complex prepared according to example 3 or 17 of the invention. Every day, the skin repairing was evaluated in comparison to the control zones, damaged and non-treated, by direct observation of the skin surface under the stereo-microscope, and by stripping studies. The effectiveness of the complex was compared to that of the wheat protein used for the preparation of said complex; the filmogenic and softening powers of the wheat protein being well-known.

The two products (protein and complexed protein) clearly and almost obviously increase the visual appearance of the horny surface; however, only the fatty acids-wheat protein complex according to the invention has an extremely significant restructuring power (neighbouring 90%), which does not limit the slowing down of the damaging effect due to the detergent, but which allows a regeneration of the whole of the integument. Thus, the treated skins are frequently in a better state after degradation and application of the aqueous solution of the complex prepared in Example 3 or 17, than before any treatment.

Thus, it is possible to affirm that the stearic and palmitic chains-wheat protein complex is an active "regenerating" cosmetic capable of equilibrating and harmonising the cohesion of the epidermis.

EXAMPLE 28

Use of a Stearic and Palmitic Acids-almond Protein Complex in Cosmetic Applications which Allow Soothing Skin Damaging Effects Linked to Sunburn The complexes prepared according to examples 4 (enzymatically) and 18 (chemically) were tested for their capacity to reduce and to calm sunburn; in fact, repeated sunburns favour an alteration of the biochemical mechanisms of the skin, by the destruction of the lipids of the cell membranes, by the fragmentation of the biological macromolecules which are indispensable to the skin reparations, and on the other hand the acceleration of the skin ageing; it being possible for the conjunction of these two phenomena to be however translated by the appearance of skin cancer.

The anti-sunburn power of the stearic and palmitic acids-almond protein complex was studied in the guinea pig whose sunburn reaction is well correlated with that of man. The irradiations of the animals were carried out with the aid of two Philipps TL 40W/12 lamps emitting between 280 and 340 nm with a peak at 315 nm. Placed at 3% within an emulsion (see composition A below), the complex prepared according to example 4 or 18 was tested in comparison to a placebo emulsion (see composition C below) and in comparison to an emulsion containing the almond polypeptide used in the complex, in a non-complexed form (see composition B below). In each case, 0.25 ml of product was administered immediately after irradiation, then 2, 5 and 24 hours after exposure. The sunburn being evaluated according to a visual quotation of 0 (no sunburn) to 4 (intense sunburn), the sunburn reducing effect was measured 2, 5, 24 and 48 hours after irradiation, in comparison to the irradiated but non-treated control areas. The results were then expressed in percentage inhibition of the sunburn.

| Phase | Ingredients | A | B | C |
|---|---|---|---|---|
| A | Complex described in example 4 or 18 | 3 | 0 | 0 |
| | Almond polypeptide | 0 | 0.75 | 0 |
| | Water | qs for 100 | qs for 100 | qs for 100 |
| B | Apricot kernel oil | 5 | 5 | 5 |
| | Isostearyl isostearate | 5 | 5 | 5 |
| | Oleyl erucate | 2 | 2 | 2 |
| | Ketostearylic alcohol | 3 | 3 | 3 |
| C | Silicone oil | 2 | 2 | 2 |
| | Parabens | 0.2 | 0.2 | 0.2 |

Preparation of the Compositions

Phases A and B are heated separately at 75° C. After a good homogenisation, B is poured into A under very vigorous stirring, the whole is then allowed to cool under slow stirring. At 30° C., phase C is then added.

Results

Moderate sunburns were effected on guinea pigs. They correspond to sunburns of index 1.5 at 24 hours. The soothing effect procured by the application of a prior art cosmetic emulsion (placebo preparation C) on the sunburns, although sensitive, remains insufficient to efficiently to combat the development of the inflammatory reaction. On the contrary, the anti-sunburn power of the complex (preparation A) is immediate (inhibition of the sunburn of about 30%, 2 hours after the application) and durable throughout the treatments (inhibition of 45%, 45% and 65% after 5, 24 and 48 hours respectively). The preparation carried out with the non-complexed almond polypeptide (preparation B) does not allow either obtaining such results.

Other results were obtained on much more pronounced provoked sunburns (sunburns index 2 at 24 hours). In this case, the efficiency of preparation A is much more pronounced compared to the efficiency obtained with other preparations.

It is therefore possible to affirm that the stearic and palmitic chains-almond protein complex used in a cosmetic formulation is an active which allows durably repairing the destructive effects of moderate even strong sunburns observed during prolonged exposures to the sun.

What is claimed is:

1. A cosmetic composition comprising a cosmetically effective amount of at least one amphiphilic complex comprising:
   the reaction product of:
   a) at least one plant component, wherein said plant component is a plant protein, a plant polypeptide, a plant polypeptide obtained by synthesis or mixtures thereof, whose average molecular weight is greater than or equal to 10,000 Daltons; and
   b) at least one fatty chain containing organic compound, having between 4 and 30 carbon atoms, wherein said fatty chain organic containing compound is selected from the group consisting of a fatty acid halide and a fatty acid anhydride; with the proviso that said fatty chain containing organic compound is not undecylenic acid;
   at least one unreacted fatty chain containing organic compound; and
   at least one cosmetically acceptable excipient.

2. The composition of claim 1, wherein said amphiphilic complex is from 0.1 to 40% by weight of the total weight of the composition.

3. The composition of claim 1, wherein said plant component has an average molecular weight between 10,000 and 1,000,000 Daltons.

4. The composition of claim 1, wherein said plant component has an average molecular weight between 20,000 and 300,000 Daltons.

5. The composition of claim 1, wherein said fatty chain containing organic compound has between 6 and 20 carbon atoms.

6. The composition of claim 1, wherein the weight ratio of said plant component to said fatty chain containing organic compound ranges from 1/1 to 1/10.

7. The composition of claim 1, wherein the weight ratio of said plant component to said fatty chain organic containing compound ranges from 1/3 to 1/5.

8. The composition of claim 1, wherein said plant component is obtained from a plant selected from the group consisting of wheat, maize, cotton, lupin, pea, broad bean, almond, beam soya, sunflower, lucerne and oat.

9. The composition of claim 1, wherein said fatty acid is selected from the group consisting of heptanoic acid, octanoic acid, decanoic acid, lauric acid, myristic acid, palmitic acid, stearic acid, ricinoleic acid, oleic acid, linoleic acid and linolenic acid.

10. The composition of claim 1, further comprising a reaction medium in which said plant component and said fatty chain containing organic compound were combined, wherein said fatty chain containing organic compound is added in excess, and the at least one unreacted fatty chain containing organic compound is neutralized.

11. The composition of claim 1, wherein said plant protein is soya protein.

12. The composition of claim 11, wherein said soya protein is grafted with at least one fatty chain selected from the group consisting of heptanoic, octanoic, decanoic, lauric, myristic, palmitic, stearic, ricinoleic, oleic, linoleic and linolenic.

13. The composition of claim 1, wherein said plant protein is wheat protein.

14. The composition of claim 13, wherein said wheat protein is grafted with at least one fatty chain selected from the group consisting of heptanoic, octanoic, decanoic, lauric, myristic, palmitic, stearic, ricinoleic, oleic, linoleic and linolenic.

15. The composition of claim 1, wherein said plant protein is almond protein.

16. The composition of claim 15, wherein said almond protein is grafted with at least one fatty chain selected from the group consisting of heptanoic, octanoic, decanoic, lauric, myristic, palmitic, stearic, ricinoleic, oleic, linoleic and linolenic.

17. The composition of claim 1, wherein said plant protein is oat protein.

18. The composition of claim 17, wherein said oat protein is grafted with at least one fatty chain selected from the group consisting of heptanoic, octanoic, decanoic, lauric, myristic, palmitic, stearic, ricinoleic, oleic, linoleic and linolenic.

19. A pharmaceutical composition comprising a pharmaceutically effective amount of at least one amphiphilic complex comprising:
   the reaction product of:
   a) at least one plant component, wherein said plant component is a plant protein, a plant polypeptide, a plant polypeptide obtained by synthesis or mixtures thereof, whose average molecular weight is greater than or equal to 10,000 Daltons; and
   b) at least one fatty chain containing organic compound, having between 4 and 30 carbon atoms, wherein said fatty chain organic containing compound is selected from the group consisting of a fatty acid halide and a fatty acid anhydride; with the proviso that said fatty chain containing organic compound is not undecylenic acid;
   at least one unreacted fatty chain containing organic compound; and
   at least one pharmaceutically acceptable excipient.

20. The composition of claim 19, wherein said amphiphilic complex is from 0.1 to 40% by weight of the total weight of the composition.

21. The composition of claim 19, wherein said plant component has an average molecular weight between 10,000 and 1,000,000 Daltons.

22. The composition of claim 19, wherein said plant component has an average molecular weight between 20,000 and 300,000 Daltons.

23. The composition of claim 19, wherein said fatty chain containing organic compound has between 6 and 20 carbon atoms.

24. The composition of claim 19, wherein the weight ratio of said plant component to said fatty chain containing organic compound ranges from 1/1 to 1/10.

25. The composition of claim 19, wherein the weight ratio of said plant component to said fatty chain organic containing compound ranges from 1/3 to 1/5.

26. The composition of claim 19, wherein said plant component is obtained from a plant selected from the group consisting of wheat, maize, cotton, lupin, pea, broad bean, almond, bean, soya, sunflower, lucerne and oat.

27. The composition of claim 19, wherein said fatty acid is selected from the group consisting of heptanoic acid, octanoic acid, decanoic acid, lauric acid, myristic acid, palmitic acid, stearic acid, ricinoleic acid, oleic acid, linoleic acid and linolenic acid.

28. The composition claim 19, fiber comprising a reaction medium in which said plant component and said fatty chain containing organic compound were combined, wherein said fatty chain containing organic compound is added in excess, and the at least one unreacted fatty chain containing organic compound is neutralized.

29. The composition of claim 19, wherein said plant protein is soya protein.

30. The composition of claim 29, wherein said soya protein is grafted with at least one fatty chain selected from the group consisting of heptanoic, octanoic, decanoic, lauric, myristic, palmitic, stearic, ricinoleic, oleic, linoleic and linolenic.

31. The composition of claim 1, wherein said plant protein is wheat protein.

32. The composition of claim 31, wherein said wheat protein is grafted with at least one fatty chain selected from the group consisting of heptanoic, octanoic, decanoic, lauric, myristic, palmitic, stearic, ricinoleic, oleic, linoleic and linolenic.

33. The composition of claim 1, wherein said plant protein is almond protein.

34. The composition of claim 33, wherein said almond protein is grafted with at least one fatty chain selected from the group consisting of heptanoic, octanoic, decanoic, lauric, myristic, palmitic, stearic, ricinoleic, oleic, linoleic and linolenic.

35. The composition of claim 1, wherein said plant protein is oat protein.

36. The composition of claim 35, wherein said oat protein is grafted with at least one fatty selected from the group consisting of heptanoic, octanoic, decanoic, lauric, myristic, palmitic, stearic, ricinoleic, oleic, linoleic and linolenic.

37. A method of cosmetic care comprising applying on skin or hair areas in need thereof a cosmetically effective amount of a cosmetic composition according to claim 1.

38. The method of claim 37, wherein said amphiphilic complex is from 0.1 to 40% by weight of the total weight of the composition.

39. The method of claim 37, wherein said plant component has an average molecular weight between 10,000 and 1,000,000 Daltons.

40. The method of claim 37, wherein said plant component has an average molecular weight between 20,000 and 300,000 Daltons.

41. The method of claim 37, wherein said fatty chain containing organic compound has between 6 and 20 carbon atoms.

42. The method of claim 37, wherein the weight ratio of said plant component to said fatty chain containing organic compound ranges from 1/1 to 1/10.

43. The method of claim 37, wherein the weight ratio of said plant component to said fatty chain containing organic compound ranges from 1/3 to 1/5.

44. The composition of claim 37, wherein said plant component is obtained from a plant selected from the group consisting of wheat, maize, cotton, lupin, pea, broad bean, almond, bean, soya, sunflower, lucerne and oat.

45. The method of claim 37, wherein said fatty chain containing organic compound is selected firm the group consisting of heptanoic acid, octanoic acid, decanoic acid, lauric acid, myristic acid, palmitic acid, stearic acid, ricinoleic acid, oleic acid, linoleic acid and linolenic acid.

46. The method of claim 37, further comprising reaction medium in which said plant component and said fatty chain containing organic compound were combined.

47. The method of claim 37, wherein said plant protein is soya protein.

48. The method of claim 47, wherein said soya protein is grafted with at least one fatty chain selected from the group consisting of heptanoic, octanoic, decanoic, lauric, myristic, palmitic, stearic, ricinoleic, oleic, linoleic and linolenic.

49. The method of claim 37, wherein said plant protein is wheat protein.

50. The method of claim 49, wherein said wheat protein is grafted with at least one fatty chain selected from the group consisting of heptanoic, octanoic, decanoic, lauric, myristic, palmitic, stearic, ricinoleic, oleic, linoleic and, linolenic.

51. The method of claim 37, wherein said plant protein is almond protein.

52. The method of claim 51, wherein said almond protein is grafted with at least one fatty chain selected from the group consisting of heptanoic, octanoic, decanoic, lauric, myristic, palmitic, stearic, ricinoleic, oleic, linoleic and linolenic.

53. The method of claim 37, wherein said plant protein is oat protein.

54. The method of claim 53, wherein said oat protein is grafted with at least one fatty chain selected from the group consisting of heptanoic, octanoic, decanoic, lauric, myristic, palmitic, stearic, ricinoleic, oleic, linoleic and linolenic.

55. A cosmetic composition comprising a cosmetically effective amount of at least one amphiphilic complex comprising:
the reaction product of:
a) at least one plant component, wherein said plant component is a plant protein, a plant polypeptide, a plant polypeptide obtained by synthesis or mixtures thereof, whose average molecular weight is greater than or equal to 10,000 Daltons; and
b) at least one fatty chain containing organic compound, having between 4 and 30 carbon atoms, wherein said fatty chain organic containing compound is selected from the group consisting of a fatty acid halide and a fatty acid anhydride; with the proviso that said fatty chain containing organic compound is not undecylenic acid;
at least one unreacted fatty chain containing organic compound; and
at least one cosmetically acceptable excipient, wherein one of said at least one cosmetically acceptable excipient comprises an oil.

56. A pharmaceutical composition comprising a pharmaceutically effective amount of at least one amphiphilic complex comprising:
the reaction product of:
a) at least one plant component, wherein said plant component is a plant protein, a plant polypeptide, a plant polypeptide obtained by synthesis or mixtures thereof, whose average molecular weight is greater than or equal to 10,000 Daltons; and
b) at least one fatty chain containing organic compound, having between 4 and 30 carbon atoms, wherein said fatty chain organic containing compound is selected from the group consisting of a fatty acid halide and a fatty acid anhydride; with the proviso that said fatty chain containing organic compound is not undecylenic acid;

at least one unreacted fatty chain containing organic compound; and at least one pharmaceutically acceptable excipient, wherein one of said at least one pharmaceutically acceptable excipient comprises an oil.

57. A cosmetic composition comprising a cosmetically effective amount of at least one amphiphilic complex comprising:

the reaction product of:
  a) at least one plant component, wherein said plant component is a plant protein, a plant polypeptide, a plant polypeptide obtained by synthesis or mixtures thereof, whose average molecular weight is greater than or equal to 10,000 Daltons; and
  b) at least one fatty chain containing organic compound, having between 4 and 30 carbon atoms, wherein said fatty chain organic containing compound is selected from the group consisting of a fatty acid halide and a fatty acid anhydride; with the proviso that said fatty chain containing organic compound is not undecylenic acid;

an unreacted part of said fatty chain containing organic compound; and at least one cosmetically acceptable excipient, wherein one of said at least one cosmetically acceptable excipient is distinct from water.

58. A pharmaceutical composition comprising a pharmaceutically effective amount of at least one amphiphilic complex comprising:

the reaction product of:
  a) at least one plant component, wherein said plant component is a plant protein, a plant polypeptide, a plant polypeptide obtained by synthesis or mixtures thereof, whose average molecular weight is greater than or equal to 10,000 Daltons; and
  b) at least one fatty chain containing organic compound, having between 4 and 30 carbon atoms, wherein said fatty chain organic containing compound is selected from the group consisting of a fatty acid halide and a fatty acid anhydride; with the proviso that said fatty chain containing organic compound is not undecylenic acid;

an unreacted part of said fatty chain containing organic compound; and at least one pharmaceutically acceptable excipient, wherein one of said at least one pharamceutically acceptable excipient is distinct from water.

59. A method of cosmetic care comprising applying on skin or hair areas in need thereof, a cosmetic composition comprising a cosmetically effective amount of at least one amphiphilic complex comprising the reaction product of wheat protein of average molecular weight of about 100,000 Daltons extracted from wheat gluten, with stearic and palmitic acids; and at least one cosmetically acceptable excipient.

60. The method of claim 59, wherein said method of cosmetic care is an anti-age face care or a shampooing.

61. A method of cosmetic care comprising applying on skin or hair areas in need thereof, a cosmetically effective amount of a cosmetic composition comprising a cosmetically effective amount of at least one amphiphilic complex comprising the reaction product of almond protein having an average molecular weight of about 30,000 Daltons with mixture of stearic and palmitic acids; and at least cosmetically acceptable excipient.

62. The method of claim 61, wherein said method of cosmetic care is shampooing or sun or after-sun care.

* * * * *